(12) United States Patent
Schambony et al.

(10) Patent No.: US 8,822,575 B2
(45) Date of Patent: Sep. 2, 2014

(54) STABILIZER MIXTURE

(75) Inventors: Simon Schambony, Ludwigshafen (DE); Hideo Yamazaki, Yokohama (JP); Greg Coughlin, Springfield, NJ (US)

(73) Assignee: BASF SE, Ludwigshafen (DE)

( * ) Notice: Subject to any disclaimer, the term of this patent is extended or adjusted under 35 U.S.C. 154(b) by 582 days.

(21) Appl. No.: 12/675,037

(22) PCT Filed: Aug. 1, 2008

(86) PCT No.: PCT/EP2008/060173
§ 371 (c)(1),
(2), (4) Date: Feb. 24, 2010

(87) PCT Pub. No.: WO2009/027180
PCT Pub. Date: Mar. 5, 2009

(65) Prior Publication Data
US 2011/0130493 A1 Jun. 2, 2011

(30) Foreign Application Priority Data
Aug. 28, 2007 (EP) .................................... 07115133

(51) Int. Cl.
*C08K 5/3435* (2006.01)
*C08K 5/00* (2006.01)
*C07D 211/58* (2006.01)
*C08K 5/3492* (2006.01)
*C07D 249/20* (2006.01)
*C08K 5/3475* (2006.01)
*C08K 5/134* (2006.01)

(52) U.S. Cl.
CPC ............ *C08K 5/1345* (2013.01); *C07D 211/58* (2013.01); *C08K 5/34926* (2013.01); *C07D 249/20* (2013.01); *C08K 5/3435* (2013.01); *C08K 5/3475* (2013.01)
USPC ................ 524/99; 524/91; 524/103; 252/403

(58) Field of Classification Search
CPC .. C08K 5/3435; C08K 5/3475; C07D 211/58; C07D 211/46; C07D 249/20
USPC ................................ 524/99, 103, 91; 252/403
See application file for complete search history.

(56) References Cited

U.S. PATENT DOCUMENTS

| 4,128,726 A | 12/1978 | Grosso et al. |
| 4,325,863 A | 4/1982 | Hinsken et al. |

(Continued)

FOREIGN PATENT DOCUMENTS

| DE | 43 16 611 | 11/1993 |
| DE | 43 16 622 | 11/1993 |

(Continued)

OTHER PUBLICATIONS

Office Action issued Nov. 9, 2012, in Chinese Patent Application No. 200880105102.2 filed Aug. 1, 2008 (English translation only).

(Continued)

*Primary Examiner* — Bijan Ahvazi
*Assistant Examiner* — Atnaf Admasu
(74) *Attorney, Agent, or Firm* — Oblon, Spivak, McClelland, Maier & Neustadt, L.L.P.

(57) ABSTRACT

The invention relates to mixtures, comprising
(a) an oligomeric compound, comprising repeat units of the general formula (I) or acid-addition salts thereof

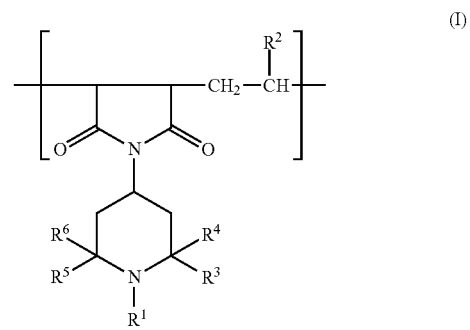

and/or
(b) a compound of the general formula (II) or acid-addition salts thereof

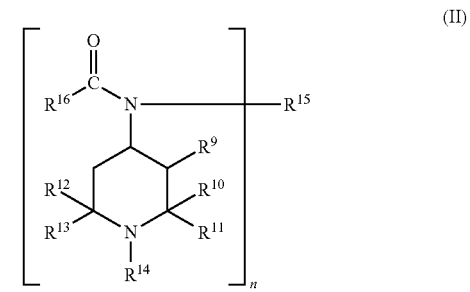

and
(c) at least one compound of the general formula (III) and

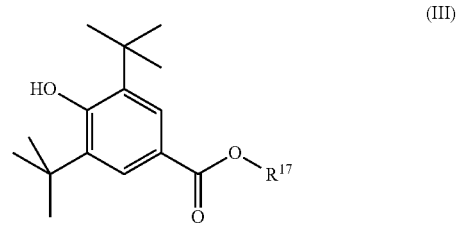

(d) optionally further additives,
and also to the use of these mixtures for the stabilization of non-living organic materials with respect to exposure to light, oxygen, and/or heat. The invention further relates to non-living organic materials, comprising at least one of these mixtures, and to articles produced therefrom. The invention further relates to a process for the stabilization of non-living organic materials, with respect to exposure to light, oxygen, and/or heat.

15 Claims, No Drawings

(56) References Cited

U.S. PATENT DOCUMENTS

| | | |
|---|---|---|
| 4,338,244 A | 7/1982 | Hinsken et al. |
| 5,175,312 A | 12/1992 | Dubs et al. |
| 5,216,052 A | 6/1993 | Nesvadba et al. |
| 5,252,643 A | 10/1993 | Nesvadba et al. |
| 5,844,029 A | 12/1998 | Prabhu et al. |
| 5,880,191 A | 3/1999 | Prabhu et al. |
| 5,965,643 A * | 10/1999 | Gugumus .................. 524/100 |
| 6,897,250 B1 | 5/2005 | Takahashi et al. |
| 2002/0013390 A1 | 1/2002 | Gugumus |
| 2004/0138350 A1 * | 7/2004 | Haremza et al. ............ 524/91 |

FOREIGN PATENT DOCUMENTS

| | | |
|---|---|---|
| DE | 43 16 876 | 11/1993 |
| DE | 198 59 096 | 6/1999 |
| DE | 199 20 590 | 11/2000 |
| DE | 101 23 732 | 11/2002 |
| EP | 0 139 919 | 5/1985 |
| EP | 0 316 582 | 5/1989 |
| EP | 0 449 685 | 10/1991 |
| EP | 0 589 839 | 3/1994 |
| EP | 0 591 102 | 4/1994 |
| EP | 0 916 335 | 5/1999 |
| GB | 2 311 292 | 9/1997 |
| JP | 10 195258 | 7/1998 |
| JP | 2003 253083 | 9/2003 |
| WO | 94 12544 | 6/1994 |
| WO | 2004 046234 | 6/2004 |
| WO | 2007 082842 | 7/2007 |

OTHER PUBLICATIONS

International Search Report issued Dec. 4, 2008 in PCT/EP08/060173 filed Aug. 1, 2008.

* cited by examiner

STABILIZER MIXTURE

The invention relates to mixtures, which comprise
(a) an oligomeric compound, comprising repeat units of the general formula (I) or acid-addition salts thereof

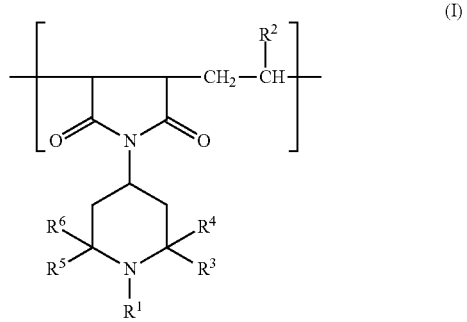

in which
$R^1$ is H, $C_2$-$C_{22}$-alkenyl, $C_1$-$C_{20}$-alkoxy, cyanomethyl, 2-hydroxyethyl, formyl, $C_2$-$C_6$-alkanoyl, benzyl, or a moiety of the formula $-CR^7$=CH$-$CO$-$OR$^8$,
$R^2$ is H, $C_1$-$C_{30}$-alkyl, or a mixture composed of $C_{14}$-$C_{28}$-alkyl groups,
$R^3$, $R^4$, $R^5$, and $R^6$, independently of one another, are identical or different $C_1$-$C_{30}$-alkyl,
$R^7$ is H, $C_1$-$C_6$-alkyl, or a moiety of the formula CO$-$OR$^8$,
$R^8$ is $C_1$-$C_{18}$-alkyl, $C_3$-$C_{15}$-cycloakyl, $C_7$-$C_{18}$-aralkyl, phenyl or tolyl,
and/or
(b) a compound of the general formula (II) or acid-addition salts thereof

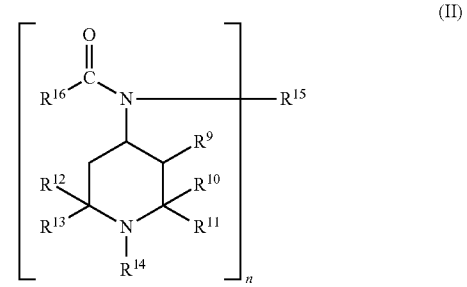

in which
n is 1 or 2,
$R^9$ is H or $C_1$-$C_4$-alkyl,
$R^{10}$, $R^{11}$, $R^{12}$, and $R^{13}$, independently of one another, are identical or different $C_1$-$C_4$-alkyl, or $R^{10}$ and $R^{11}$ or $R^{12}$ and $R^{13}$ together are a tetramethylene group or pentamethylene group,
$R^{14}$ is H, $C_1$-$C_{30}$-alkyl, or $C_2$-$C_{22}$-alkenyl, or unsubstituted or $C_1$-$C_4$-alkyl-, halogen-, $C_1$-$C_4$-alkoxy-, methylenedioxy-, ethylenedioxy-, and/or di-$C_1$-$C_4$-alkylamino-substituted $C_7$-$C_{12}$-phenylalkyl, $C_1$-$C_{22}$-alkanoyl, $C_2$-$C_3$-cyanoalkyl, $C_1$-$C_{22}$-hydroxyalkyl or $C_2$-$C_{22}$-aminoalkyl,
$R^{16}$ is H or $C_1$-$C_{30}$-alkyl,
and
if n=1—
$R^{15}$ is H, $C_1$-$C_{22}$-alkyl, $C_2$-$C_{22}$-alkenyl, $C_3$-$C_{12}$-cycloalkyl or bicycloalkyl, or cyano-, hydroxyl-, or carbo-$C_1$-$C_4$-alkoxy-substituted $C_2$-$C_{22}$-alkyl, or ether-oxygen-, nitrogen-, or sulfur-interrupted $C_4$-$C_{22}$-alkyl, or unsubstituted or $C_1$-$C_4$-alkyl-, halogen-, $C_1$-$C_4$-alkoxy-, methylenedioxy-, ethylenedioxy-, or di-$C_1$-$C_4$-alkylamino-substituted $C_7$-$C_{22}$-phenyl- or diphenylalkyl, or unsubstituted or $C_1$-$C_4$-alkyl- or carbo-$C_1$-$C_4$-alkoxy-substituted phenyl, or a moiety of the general formula (IV)

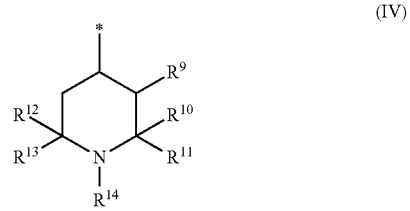

or $C_1$-$C_{22}$-alkyl comprising heterocyclic moieties,
or
if n=2—
$R^{15}$ is $C_2$-$C_{22}$-alkylene, $C_5$-$C_{22}$-cycloalkylene, $C_8$-$C_{14}$-phenylalkylene, or phenylene, or ether-oxygen-, nitrogen-, or sulfur-interrupted $C_4$-$C_{30}$-alkylene, or $C_4$-$C_{30}$-alkylene interrupted by 5- or 6-membered heterocyclic moieties,
and
(c) at least one compound of the general formula (III)

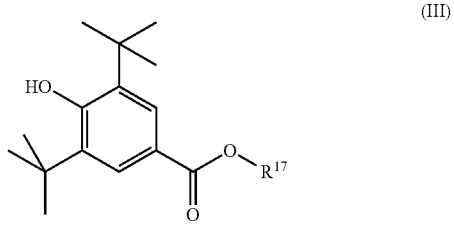

in which
$R^{17}$ is $C_1$-$C_{20}$-alkyl or aryl,
and
optionally further additives.

The present invention moreover describes processes for the stabilization of non-living organic materials, in particular plastics, with respect to exposure to light, oxygen, and/or heat, using this mixture. The invention further relates to articles which are produced from non-living organic materials thus stabilized.

Further embodiments of the present invention are given in the claims, in the description, and in the examples. The above-mentioned features, and the features that will be explained below, of the inventive subject matter can, of course, be used not only in the respective combination specifically stated but also in other combinations, without exceeding the scope of the invention. Preference and, respectively, a high level of preference are also particularly given to those embodiments of the present invention in which all of the features of the inventive subject matter have the preferred or, respectively, the very preferred definitions.

Non-living organic materials, in particular plastics, are known to undergo very rapid irreversible damage especially through exposure to light, oxygen, and/or heat. This irreversible damage usually takes the form of yellowing, discoloration, cracking, or embrittlement of the material. The use of light stabilizers and of other stabilizers is therefore intended to provide satisfactory protection from irreversible damage to non-living organic material due to light, oxygen, and/or heat.

Derivates of 2,2,6,6-tetraalkylpiperidine, called HALS (Hindered Amine Light Stabilizers) have now been used commercially for about three decades in the form of light stabilizers and other stabilizers, in particular for plastics and coatings.

WO 2004/046234 A2 discloses stabilizer mixtures which comprise a UV absorber and at least one further component, selected from a group of five classes of compound. UV absorbers mentioned are inter alia benzoates, and sterically hindered amines can also be one of the further components. No combination composed of hydroxybenzoates with HALS compounds is disclosed.

JP 2003253083 describes a propylene-ethylene block copolymer which comprises from 0.03 to 3% of a mixture composed of alkyl benzoate and HALS.

JP 10195258 discloses agriculture foils composed of polyolefins, stabilized with HALS and with benzoates.

U.S. Pat. No. 6,897,250 B1 describes automobile parts composed of thermoplastic elastomers, which comprise from 0.001 to 10% of alkyl benzoates and from 0.1 to 0.5% of HALS.

Although these compounds and mixtures have been proven outstandingly successful in previous commercial use, there is nevertheless scope for improvements, particularly relating to resistance to light with high UV content.

It was therefore an object of the present invention to provide mixtures which provide improved stabilization of non-living organic material with respect to light with high UV content and/or high light intensity. A further object of the invention was to provide mixtures which offer a high degree of stabilization and which are based on starting materials that are easy to obtain. A further subobject of the present invention was to provide mixtures which provide improved stability of non-living organic material with respect to oxygen or heat.

The mixtures described in the introduction have accordingly been found.

For the purposes of this invention, expressions of the type $C_a$-$C_b$ indicate chemical compounds or substituents having a certain number of carbon atoms. The number of carbon atoms can be selected from the entire range from a to b, inclusive of a and b, and a is at least 1, and b is always greater than a. Further specification of the chemical compounds or of the substituents is achieved via expressions of the type $C_a$-$C_b$-V. V here is a class of chemical compound or class of substituent, for example alkyl compounds or alkyl substituents.

Halogen is fluorine, chlorine, bromine, or iodine, preferably fluorine, chlorine, or bromine, particularly preferably fluorine or chlorine.

The individual definitions of various collective terms given are as follows:

$C_1$-$C_{30}$-alkyl: straight-chain or branched hydrocarbon moieties having up to 30 carbon atoms, for example $C_1$-$C_{18}$-alkyl, $C_1$-$C_{10}$-alkyl, or $C_{11}$-$C_{20}$-alkyl, preferably $C_1$-$C_{10}$-Alkyl, for example $C_1$-$C_6$-alkyl, $C_1$-$C_4$-alkyl, $C_1$-$C_3$-alkyl, such as methyl, ethyl, n-propyl, isopropyl, or $C_4$-$C_6$-alkyl, n-butyl, sec-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethyl-propyl, 1,2,2-tri-methyl propyl, 1-ethyl-1-methylpropyl, 1-ethyl-2-methylpropyl, or $C_7$-$C_{10}$-alkyl, such as heptyl, octyl, 2-ethylhexyl, 2,4,4-trimethylpentyl, 1,1,3,3-tetramethylbutyl, nonyl or decyl (e.g. 2-propylheptyl), and also their isomers.

$C_2$-$C_{22}$-alkenyl: unsaturated, straight-chain, or branched hydrocarbon moieties having from 2 to 22 carbon atoms and having at least one double bond, preferably having one double bond, in any desired position, for example $C_2$-$C_{10}$-alkenyl or $C_{11}$-$C_{22}$-alkenyl, preferably $C_2$-$C_{10}$-alkenyl such as $C_2$-$C_4$-Alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, or $C_5$-$C_6$-alkenyl, such as 1-pentenyl, 2-pentenyl, 3-pentenyl, 4-pentenyl, 1-methyl-1-butenyl, 2-methyl-1-butenyl, 3-methyl-1-butenyl, 1-Methyl-2-butenyl, 2-Methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-di-methyl-1-butenyl, 1,2-dimethyl-2-butenyl, 1,2-dimethyl-3-butenyl, 1,3-di-methyl-1-butenyl, 1,3-dimethyl-2-butenyl, 1,3-dimethyl-3-butenyl, 2,2-di-methyl-3-butenyl, 2,3-dimethyl-1-butenyl, 2,3-dimethyl-2-butenyl, 2,3-di-methyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, or else $C_7$-$C_{10}$-alkenyl, such as the isomers of heptenyl, octenyl, nonenyl or decenyl.

$C_3$-$C_{15}$-cycloalkyl: monocyclic, saturated hydrocarbon groups having from 3 up to 15 carbon ring members, preferably $C_3$-$C_8$-Cycloalkyl such as cyclopropyl, cyclobutyl, cyclopentyl, cyclohexyl, cycloheptyl or cyclooctyl or else a saturated or unsaturated cyclic system, e.g. norbornyl or norbornenyl. $C_5$-$C_6$-cycloalkyl is particularly preferred. $C_1$-$C_{22}$-alkanoyl: a straight-chain or branched alkyl group having from 1 to 22 carbon atoms (as mentioned above) which have linkage by way of a carbonyl group (—CO—), for example $C_1$-$C_{11}$-alkanoyl or $C_{12}$-$C_{22}$-alkanoyl, preferably $C_1$-$C_{11}$-alkanoyl, such as $C_1$-$C_6$-alkanoyl, such as formyl, acetyl, n- or isopropionyl, n-, iso-, sec- or tert-butanoyl, n-, iso-, sec- or tert-pentanoyl, hexanoyl, or $C_9$-$C_{12}$-alkanoyl, such as n- or isononanoyl, or n-dodecanoyl.

Aryl: a mono- to trinuclear aromatic ring system comprising from 6 to 14 carbon ring members, e.g. phenyl, hydroxyphenyl, naphthyl, or anthracenyl, preferably a mono- to binuclear, particular preferably a mononuclear, aromatic ring system.

Substituted aryl moieties: aryl moieties which can have substitution at any desired position, but not more than 5 times, preferably not more than 4 times, particularly preferably not more than 3 times, and very particularly preferably twice or once, by $C_1$-$C_{20}$-alkyl or by hydroxy.

Aralkyl: aryl-substituted alkyl moieties. Examples are naphthylmethyl, diphenylmethyl or methylbenzyl, in particular 1-phenylethyl, 2-phenylethyl, 1-phenylpropyl, 2-phenylpropyl, 3-phenylpropyl, 2-phenyl-prop-2-yl, 4-phenylbutyl, 2,2-dimethyl-2-phenylethyl, 5-phenylamyl, 10-phenyldecyl, 12-phenyldodecyl, or especially benzyl. Preferably $C_7$-$C_{18}$- aralkyl: aryl-substituted alkyl moieties with 7 to 18 hydrocarbon atoms. Tolyl moieties that can be used are ortho-, meta-, and especially p-tolyl.

Heterocyclic moieties: five- to twelve-membered, preferably five- to nine-membered, particularly preferably five- to six-membered, ring systems having oxygen atoms, nitrogen atoms, and/or sulfur atoms and, if appropriate, having a plurality of rings, examples being furyl, thiophenyl, pyrryl, pyridyl, imidazoyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl, or tert-butylthiophenyl.

$C_1$-$C_{20}$-alkoxy is defined as a straight-chain or branched alkyl group having from 1 to 20 carbons atoms (as mentioned above) linked by way of an oxygen atom (—O—), for example $C_1$-$C_{10}$-alkoxy, such as n-hexoxy, isohexoxy, n-octoxy, 2-ethylhexoxy and isooctoxy, and also methoxy, ethoxy, n-propoxy, isopropoxy, n-butoxy, isobutoxy, sec-butoxy, tert-butoxy, n-pentoxy, n-nonoxy, n-decoxy, or $C_{11}$-$C_{20}$-Alkoxy such as n-undecoxy and n-dodecoxy, preferably $C_1$-$C_{10}$-alkyloxy, particularly preferably $C_1$-$C_3$-alkoxy such as methoxy, ethoxy, propoxy.

$C_1$-$C_{22}$-alkylene: straight-chain or branched hydrocarbon moieties having from 1 to 22 carbon atoms, for example $C_2$-$C_{10}$-alkylene or $C_{11}$-$C_{22}$-alkylene, preferably $C_2$-$C_{10}$-alkylene, in particular methylene, dimethylene, trimethylene, tetramethylene, pentamethylene, or hexamethylene.

$C_1$-$C_{22}$-cycloalkylene: straight-chain or branched hydrocarbon moieties having from 5 to 22 carbon atoms, where one alkylene moiety has interruption by a cycloalkyl group, i.e. two hydrogens of the cycloalkyl group have been replaced by alkylene moieties.

$C_8$-$C_{14}$-phenylalkylene: straight-chain or branched hydrocarbon moieties having from 8 to 14 carbon atoms, where the alkylene chain has interruption by a phenylene group.

$C_1$-$C_{22}$-hydroxyalkyl: a $C_1$-$C_{22}$-alkyl moiety substituted at any desired position by a hydroxy group.

$C_1$-$C_{22}$-aminoalkyl: a $C_1$-$C_{22}$-alkyl moiety substituted at any desired position by an amino group.

Each of the individual substituents $R^1$ to $R^{17}$ listed can have interruption at any desired position by one or more heteroatoms, where the number of these heteroatoms is not more than 10, preferably not more than 8, very particularly preferably not more than 5, and in particular not more than 3 and/or each of the substituents IR, to $R^{17}$ can have substitution at any desired position, but not more than five times, preferably not more than four times, and particularly preferably not more than three times by $C_1$-$C_{30}$-alkyl, $C_1$-$C_{20}$-alkoxy, aryl, heterocyclic moieties, heteroatoms, or halogen, and these likewise can have substitution at most twice, preferably at most once by the groups mentioned or by substituted aryl moieties.

The definition of the classes of compound mentioned in this group: $C_1$-$C_{30}$-alkyl, $C_1$-$C_{20}$-alkoxy, aryl and heterocyclic moieties, is as mentioned above.

Heteroatoms are preferably oxygen, nitrogen, sulfur, or phosphorus.

Acid-addition salts are the salts of the respective compounds with mineral acids, for example HCl, or with organic acids, for example acetic acid.

Component (a) in the inventive mixtures can comprise one or more different oligomeric compounds, comprising repeat units of the general formula (I), or their acid-addition salts.

Components (b) in the inventive mixtures can moreover comprise one or more compounds of the general formula (II) or their acid-addition salts.

Components (c) in the inventive mixtures can moreover comprise one or more different compounds of the general formula (III), and component (d) in the inventive mixtures can optionally comprise one or more additives.

The average molecular weight of the oligomeric compounds of the component (a) is generally from 1000 to 50 000, preferably from 1500 to 10 000, and in particular from 3000 to 5000. The molecular weights stated are number-average molecular weights.

The average number of repeat units in the oligomeric compounds is from 3 to 100, preferably from 4 to 30, in particular from 5 to 10.

The moiety $R^1$ is preferably H, $C_1$-$C_6$-alkyl, formyl, acyl, $C_1$-$C_6$-alkoxy, benzyl, or a moiety of the formula —CH=CH—CO—R', where R' is $C_1$-$C_6$-alkyl, in particular methyl or ethyl. $R^1$ is particularly preferably H, methyl, or $C_1$-$C_6$-alkoxy, in particular H.

The moiety $R^2$ ist preferably $C_{12}$-$C_{30}$-alkyl. The moiety $R^2$ can moreover be a mixture composed of $C_{14}$-$C_{28}$-alkyl groups, preferably $C_{16}$-$C_{24}$-alkyl, in particular $C_{18}$-$C_{22}$-alkyl. $R^2$ is preferably linear alkyl groups.

The presence of a mixture of alkyl groups for $R^2$ is to be understood to mean that, taking a statistical average over the entire number of all of the alkyl groups present, two particular alkyl groups which do not differ by more than two carbon atoms respectively make up at least 30%, preferably respectively at least 40%, of this mixture. In particular, these are mixtures of three particular alkyl groups, for example octadecyl, eicosyl, and docosyl, where two of these groups which differ by 2 carbon atoms make up more than 40% of the mixture and the third group makes up from 3 to 18% of the mixture; the mixture here can comprise very small amounts of further alkyl groups having somewhat fewer than 18 or somewhat more than 22 carbon atoms, these amounts usually being less than 2%.

The moieties $R^3$, $R^4$, $R^5$, and $R^6$ are preferably $C_1$-$C_4$-alkyl, particularly preferably methyl, and it is particularly preferable that each of the moieties $R^3$, $R^4$, $R^5$, and $R^6$ is methyl.

Particular preference is given to an oligomeric compound of component (a) which is an oligomeric compound having the repeat unit (Ia)

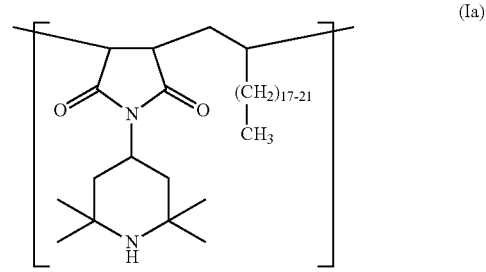

(Ia)

and having a number-average molar mass of from 3000 to 4000 g/mol.

A compound of this type is obtainable as Uvinul® 5050 H from BASF Aktiengesellschaft, Ludwigshafen, Germany.

Particularly preferred oligomeric compounds of components (a) are those in which a maximum number, in particular all, of the substituents, symbols, and indices assume their preferred or particularly preferred definition.

The oligomeric compounds of component (a) can, if the compounds are not commercially available, be prepared by the methods stated in WO 94/12544.

Among the compounds of the general formula (II) of component (b), preference is given to those in which the definitions of the symbols and indices are as follows:

$R^{14}$ is preferably H, formyl, acyl, or benzyl, particularly preferably H, methyl, formyl, acyl, or benzyl, in particular H.

$R^{10}$, $R^{11}$, $R^{12}$, and $R^{13}$ are preferably $C_1$-$C_4$-alkyl, particularly preferably methyl, and it is particularly preferable that all of the moieties $R^{10}$, $R^{11}$, $R^{12}$, and $R^{13}$ are methyl.

$R^{16}$ is preferably H.

n is preferably 2.

If n=2, $R^{15}$ is preferably $C_2$-$C_{22}$-alkylene, particularly preferably $C_4$-$C_{10}$-alkylene, very particularly preferably $C_6$-$C_8$-alkylene, in particular C6-alkylene.

Particular preference is given, as compound of the general formula (II) of component (b), to the compound (IIa)

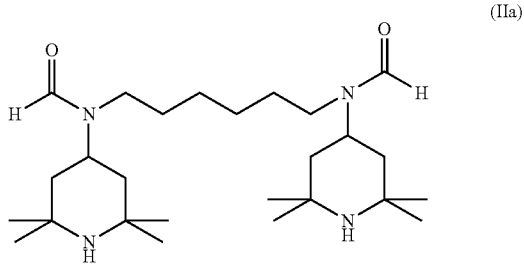

(IIa)

which is commercially obtainable as Uvinul® 4050 H from BASF Aktiengesellschaft, Ludwigshafen, Germany.

Particularly preferred compounds of the general formula (II) of component (b) are those in which a maximum number, in particular all, of the substituents, symbols, and indices assume their preferred or particularly preferred definition.

Compounds of the general formula (II), in particular components of the formula (IIa), can, if they are not commercially available, be prepared by the methods described in EP-A 0 316 582 and GB 2311292.

Among the compounds of the general formula (III) of component (c), preference is given to those in which the definitions of the symbols and indices are as follows:

$R^{17}$ is preferably $C_{10}$-$C_{20}$-alkyl or a substituted aryl moiety, very preferably $C_{14}$-$C_{18}$-alkyl or a substituted phenyl moiety, in particular a $C_{16}$-alkyl moiety ($C_{16}H_{33}$) or disubstituted phenyl moiety. $R^{17}$ is very particularly preferably either a linear $C_{16}$-alkyl moiety or a 2,4-di-tert-butylphenyl moiety.

Compounds of the general formula (III) can, if they are not commercially available, be prepared by familiar methods known to the person skilled in the art, as described by way of example in the specifications U.S. Pat. No. 4,128,726 and EP 139919.

The ratio by weight of components (a) and (b) in the inventive mixtures is generally, if the two components are present, from 5:1 to 1:5, preferably from 2:1 to 1:2, particularly preferably from 1.2:1 to 1:1.2, and particular preference is given to a mixture in which the ratio by weight is about 1:1.

If no component (b) is present, the ratio by weight of components (a) and (c) in the inventive mixtures is generally from 10:1 to 1:2, preferably from 5:1 to 1:1, particularly preferably from 2:1 to 1:1, and particular preference is given to a mixture in which the ratio by weight is about 2:1.

If no component (a) is present, the ratio by weight of components (b) and (c) in the inventive mixtures is generally from 10:1 to 1:2, preferably from 5:1 to 1:1, particularly preferably from 2:1 to 1:1, and particular preference is given to a mixture in which the ratio by weight is about 2:1.

If component (a) and component (b) are present, the ratio by weight of the entirety of components (a) and (b) to component (c) in the inventive mixtures is generally from 10:1 to 1:2, preferably from 5:1 to 1:1, particularly preferably from 2:1 to 1:1, and particular preference is given to a mixture in which the ratio by weight is about 2:1.

The inventive mixtures can be prepared by familiar processes known to the person skilled in the art.

A possible preferred method adds component (c) to a melt of component (a) and/or (b), homogenizes the mixture, converts it to the desired shape, for example pastilles, and allows it to cool.

However, it is also possible to mix solutions of components (c) and (a) and/or (b), and then to remove the solvent(s).

Another possibility is to combine the products which, if appropriate, have been previously ground. The mixture can also, if appropriate, be converted to a suitable form, for example via pelletization, after the mixing process.

The invention therefore also provides an appropriate process for the preparation of the inventive mixtures.

The following combinations of compounds of components (c) and (a), and/or (b) are particularly preferred:
the combination of the compounds (IIIa) or (IIIb) with (Ia), (IIIa) or (IIIb) with (IIa), and also of a mixture composed of (Ia) and (IIb) with (IIIa) or (IIIb)

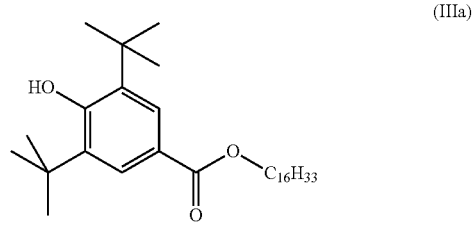

(IIIa)

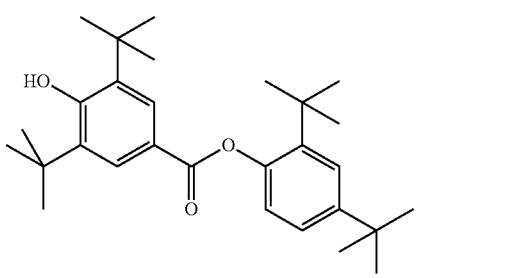

(IIIb)

Particular preference is given to the combination of the compound (Ia) with the compound (IIIa), and to the combination of the compounds (Ia) and (IIIb).

The inventive mixtures have excellent suitability for use as stabilizers for the stabilization of non-living organic material with respect to exposure to light, oxygen, and heat. The inventive mixtures are added to the non-living organic materials to be stabilized, the concentration added generally being sufficient to achieve the desired stabilizing action. The concentration added of the inventive mixtures prior to, during, or after the production of the non-living organic material is preferably from 0.01 to 5% by weight, with preference from 0.02 to 1% by weight, based on the non-living organic material.

The form in which the inventive mixture is added to the non-living organic material to be protected can be that of a prefabricated mixture of components (a) and/or (b), and (c), but it is equally possible to add components (a) and/or (b), and (c) separately to the material to be protected, in which case the mixture is not produced until it is within the material to be protected. Separate addition of components (a) and/or (b), and (c) can take place simultaneously or non-simultaneously, and the sequence here is generally not important.

Examples of non-living organic material are cosmetic preparations, such as ointments and lotions, pharmaceutical formulations, such as pills and suppositories, photographic recording material, such as photographic emulsions, or precursors of plastics and coatings, but in particular plastic and coatings themselves. Articles can be produced from non-living organic material.

The invention also provides non-living organic material stabilized with respect to exposure to light, oxygen, and heat, in particular plastics and coatings, where the material comprises the inventive mixtures, preferably at the concentrations stated above.

Any of the known apparatuses and methods for mixing to incorporate stabilizing compositions or other additives into polymers can be used for the mixing of the inventive mixture, especially with plastics.

The inventive mixture optionally additionally comprises, as component (d), or the non-living organic material to be stabilized by the mixture optionally additionally comprises, at least one further light stabilizer and/or further (co)stabilizers. Examples of suitable light stabilizers and further (co) stabilizers are those selected from the groups a) to s):
a) 4,4-diarylbutadienes,
b) cinnamic esters,
c) benzotriazoles,
d) hydroxybenzophenones,
e) diphenylcyanoacrylates,
f) oxamides,
g) 2-phenyl-1,3,5-triazines;
h) antioxidants,
i) nickel compounds,
j) sterically hindered amines which differ from the compounds of the general formulae (I) and (II)
k) metal deactivators,
l) phosphites and phosphonites,
m) hydroxylamines,
n) nitrones,
o) amine oxides,
p) benzofuranones and indolinones,
q) thiosynergists,
r) peroxide-destroying compounds, and
s) basic costabilizers.

The group a) of the 4,4-diarylbutadienes includes, for example, compounds of the formula (aa)

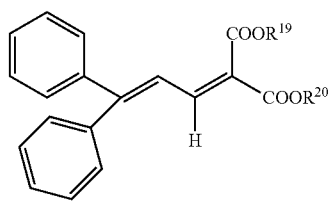

(aa)

The compounds are known from EP-A-916 335. The substituents $R^{19}$ and $R^{20}$ are, independently of one another, identical or different, preferably being $C_1$-$C_8$-alkyl and $C_5$-$C_8$-cycloalkyl.

The group b) of the cinnamic esters includes, for example, 2-isoamyl 4-methoxy-cinnamate, 2-ethylhexyl 4-methoxy-cinnamate, methyl α-(methoxycarbonyl)cinnamate, methyl α-cyano-β-methyl-p-methoxycinnamate, butyl α-cyano-β-methyl-p-methoxy-cinnamate, and methyl α-(methoxycarbonyl)-p-methoxycinnamate.

The group c) of the benzotriazoles includes, for example, 2-(2'-hydroxyphenyl)benzo-triazoles, such as 2-(2'-hydroxy-5'-methyl phenyl)benzotriazole, 2-(3',5'-di(tert-butyl)-2'-hydroxyphenyl)benzotriazole, 2-(5'-(tert-butyl)-2'-hydroxyphenyl)benzotriazole, 2-(2'-hydroxy-5'-(1,1,3,3-tetramethylbutyl)phenyl)benzotriazole, 2-(3',5'-di(tert-butyl)-2'-hydroxyphenyl)-5-chlorobenzotriazole, 2-(3'-(tert-butyl)-2'-hydroxy-5'-methylphenyl)-5-chlorobenzotriazole, 2-(3'-(sec-butyl)-5'-(tert-butyl)-2'-hydroxyphenyl)benzotriazole, 2-(2'-hydroxy-4'-octyloxyphenyl)benzotriazole, 2-(3',5'-di(tert-amyl)-2'-hydroxyphenyl)-benzotriazole, 2-(3',5'-bis(α,α-dimethylbenzyl)-2'-hydroxyphenyl)benzotriazole, 2-(3'-(tert-butyl)-2'-hydroxy-5'-(2-octyloxycarbonylethyl)phenyl)-5-chlorobenzotriazole, 2-(3'-(tert-butyl)-5'-[2-(2-ethylhexyloxy)carbonylethyl]-2'-hydroxyphenyl)-5-chlorobenzo-triazole, 2-(3'-(tert-butyl)-2'-hydroxy-5'-(2-methoxycarbonylethyl)phenyl)-5-chlorobenzo-triazole, 2-(3'-(tert-butyl)-2'-hydroxy-5'-(2-methoxycarbonylethyl)phenyl)benzotriazole, 2-(3'-(tert-butyl)-2'-hydroxy-5'-(2-octyloxycarbonylethyl)phenyl)benzotriazole, 2-(3'-(tert-butyl)-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-(tert-butyl)-2'-hydroxy-5'-(2-isooctyloxycarbonylethyl)phenyl)benzotriazole, 2,2'-methylenebis[4-(1,1,3,3-tetramethylbutyl)-6-(benzotriazol-2-yl)phenol], the product of esterification of 2-[3'-(tert-butyl)-5'-(2-methoxycarbonylethyl)-2'-hydroxyphenyl]-2H-benzotriazole with polyethylene glycol 300, $[R—CH_2CH_2—COO(CH_2)_3]_2$, where R=3'-(tert-butyl)-4'-hydroxy-5'-(2H-benzotriazol-2-yl)phenyl, and mixtures thereof.

The group d) of the hydroxybenzophenones includes, for example, 2-hydroxybenzo-phenones, such as 2-hydroxy-4-methoxybenzophenone, 2,2'-dihydroxy-4-methoxy-benzophenone, 2,4-dihydroxybenzophenone, 2,2',4,4'-tetrahydroxybenzophenone, 2,2'-dihydroxy-4,4'-dimethoxybenzophenone, 2,2'-dihydroxy-4,4'-dimethoxybenzo-phenone, 2-hydroxy-4-(2-ethylhexyloxy)benzophenone, 2-hydroxy-4-(n-octyloxy)benzo-phenone, 2-hydroxy-4-methoxy-4'-methylbenzophenone, 2-hydroxy-3-carboxybenzo-phenone, 2-hydroxy-4-methoxybenzophenone-5-sulfonic acid and its sodium salt, and 2,2'-dihydroxy-4,4'-dimethoxybenzophenone-5,5'-disulfonic acid and its sodium salt.

The group e) of the diphenylcyanoacrylates includes, for example, ethyl 2-cyano-3,3-diphenylacrylate, which, for example, is obtainable commercially as Uvinul® 3035 from BASF AG, Ludwigshafen, 2-ethylhexyl 2-cyano-3,3-diphenylacrylate, which, for example, is obtainable commercially as Uvinul® 3039 from BASF AG, Ludwigshafen, and 1,3-bis[(2'-cyano-3',3'-diphenylacryloyl)oxy]-2,2-bis{[(2'-cyano-3',3'-diphenyl-acryloyl)oxy]methyl}propane, which, for example, is obtainable commercially as Uvinul® 3030 from BASF AG, Ludwigshafen.

The group f) of the oxamides includes, for example, 4,4'-dioctyloxyoxanilide, 2,2'-di-ethoxyoxanilide, 2,2'-dioctyloxy-5,5'-di(tert-but)oxanilide, 2,2'-didodecyloxy-5,5'-di(tert-but)oxanilide, 2-ethoxy-2'-ethyloxanilide, N,N'-bis(3-dimethylaminopropyl)oxamide, 2-ethoxy-5-(tert-butyl)-2'-ethoxanilide and its mixture with 2-ethoxy-2'-ethyl-5,4'-di(tert-but)oxanilide, and also mixtures of ortho- and para-methoxy-disubstituted oxanilides and mixtures of ortho- and para-ethoxy-disubstituted oxanilides.

The group g) of the 2-phenyl-1,3,5-triazines includes, for example, 2-(2-hydroxy-phenyl)-1,3,5-triazines, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-di-hydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethyl-phenyl)-1,3,5-triazine, 2-[2-hydroxy-4-(2-hydroxy-3-(butyloxy)propoxy)phenyl]-4,6-bis(2,4-dimethyl)-1,3,5-triazine, 2-[2-hydroxy-4-(2-hydroxy-3-(octyloxy)propoxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-(dodecyloxy)propoxy)phenyl]-4,6-bis(2,4-dimethylphenyl)-1,3,5-triazine, 2-(2-hydroxy-4-hexyloxyphenyl)-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine and 2-(2-hydroxyphenyl)-4-(4-methoxyphenyl)-6-phenyl-1,3,5-triazine.

The group h) of the antioxidants comprises, for example: alkylated monophenols, for example 2,6-di(tert-butyl)-4-methylphenol, 2-(tert-butyl)-4,6-dimethylphenol, 2,6-di(tert-butyl)-4-ethylphenol, 2,6-di(tert-butyl)-4-(n-butyl)phenol, 2,6-di(tert-butyl)-4-isobutylphenol, 2,6-dicyclopentyl-4-methylphenol, 2-(α-methyl-cyclohexyl)-4,6-dimethylphenol, 2,6-dioctadecyl-4-methylphenol, 2,4,6-tricyclo-hexylphenol, 2,6-di(tert-butyl)-4-methoxymethylphenol, unbranched nonylphenols or nonylphenols which are branched in the side chain, such as, for example, 2,6-dinonyl-4-methylphenol, 2,4-dimethyl-6-(1-methylundec-1-yl)phenol, 2,4-dimethyl-6-(1-methyl-heptadec-1-yl)phenol, 2,4-dimethyl-6-(1-methyltridec-1-yl)phenol and mixtures thereof.

Alkylthiomethylphenols, for example 2,4-dioctylthiomethyl-6-(tert-butyl)phenol, 2,4-dioctylthiomethyl-6-methylphenol, 2,4-dioctylthiomethyl-6-ethylphenol and 2,6-di-dodecylthiomethyl-4-nonylphenol.

Hydroquinones and alkylated hydroquinones, for example 2,6-di(tert-butyl)-4-methoxyphenol, 2,5-di(tert-butyl)hydroquinone, 2,5-di(tert-amyl)hydroquinone, 2,6-diphenyl-4-octadecyloxyphenol, 2,6-di(tert-butyl)hydroquinone, 2,5-di(tert-butyl)-4-hydroxyanisole, 3,5-di(tert-butyl)-4-hydroxyanisole, 3,5-di(tert-butyl)-4-hydroxyphenyl stearate and bis(3,5-di(tert-butyl)-4-hydroxyphenyl) adipate.

Tocopherols, for example α-tocopherol, β-tocopherol, γ-tocopherol, δ-tocopherol and mixtures thereof (vitamin E).

Hydroxylated thiodiphenyl ethers, for example 2, 2'-thiobis(6-(tert-butyl)-4-methyl-phenol), 2,2'-thiobis(4-octylphenol), 4,4'-thiobis(6-(tert-butyl)-3-methylphenol), 4,4'-thiobis(6-(tert-butyl)-2-methylphenol), 4,4'-thiobis(3,6-di(sec-amyl)phenol) and 4,4'-bis(2,6-dimethyl-4-hydroxyphenyl) disulfide.

Alkylidenebisphenols, for example 2, 2'-methylenebis(6-(tert-butyl)-4-methylphenol), 2,2'-methylenebis(6-(tert-butyl)-4-ethylphenol), 2,2'-methylenebis[4-methyl-6-α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di(tert-butyl)phenol), 2,2'-ethylidenebis(4,6-di(tert-butyl)phenol), 2,2'-ethylidenebis(6-(tert-butyl)-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di(tert-butyl)phenol), 4,4'-methylenebis(6-(tert-butyl)-2-methylphenol), 1,1-bis(5-(tert-butyl)-4-hydroxy-2-methylphenyl)butane, 2,6-bis(3-(tert-butyl)-5-methyl-2-hydroxybenzyl)-4-methylphenol, 1,1,3-tris(5-(tert-butyl)-4-hydroxy-2-methylphenyl)butane, 1,1-bis(5-(tert-butyl)-4-hydroxy-2-methylphenyl)-3-(n-dodecylmercapto)butane, ethylene glycol bis[3,3-bis(3-(tert-butyl)-4-hydroxyphenyl)butyrate], bis(3-(tert-butyl)-4-hydroxy-5-methylphenyl)dicyclopentadiene, bis[2-(3'-(tert-butyl)-2-hydroxy-5-methylbenzyl)-6-(tert-butyl)-4-methylphenyl]terephthalate, 1,1-bis(3,5-dimethyl-2-hydroxyphenyl)butane, 2,2-bis(3,5-di(tert-butyl)-4-hydroxyphenyl)propane, 2,2-bis(5-(tert-butyl)-4-hydroxy-2-methylphenyl)-4-(n-dodecylmercapto)butane and 1,1,5,5-tetra(5-(tert-butyl)-4-hydroxy-2-methylphenyl)pentane.

Benzyl compounds, for example 3, 5,3',5'-tetra(tert-butyl)-4,4'-dihydroxydibenzyl ether, octadecyl 4-hydroxy-3,5-dimethylbenzylmercaptoacetate, tridecyl 4-hydroxy-3,5-di(tert-butyl)benzylmercaptoacetate, tris(3,5-di(tert-butyl)-4-hydroxybenzyl)amine, 1,3,5-tri(3,5-di(tert-butyl)-4-hydroxybenzyl)-2,4,6-trimethylbenzene, di(3,5-di(tert-butyl)-4-hydroxybenzyl) sulfide, isooctyl 3,5-di(tert-butyl)-4-hydroxybenzylmercaptoacetate, bis(4-(tert-butyl)-3-hydroxy-2,6-dimethylbenzyl)dithiol terephthalate, 1,3,5-tris(3,5-di(tert-butyl)-4-hydroxybenzyl) isocyanurate, 1,3,5-tris(4-(tert-butyl)-3-hydroxy-2,6-dimethylbenzyl) isocyanurate, 3,5-di(tert-butyl)-4-hydroxybenzyl dioctadecyl phosphate and 3,5-di(tert-butyl)-4-hydroxybenzyl monoethyl phosphate, calcium salt.

Hydroxybenzylated malonates, for example dioctadecyl 2,2-bis(3,5-di(tert-butyl)-2-hydroxybenzyl)malonate, dioctadecyl 2-(3-(tert-butyl)-4-hydroxy-5-methyl-benzyl)malonate, didodecylmercaptoethyl 2,2-bis(3,5-di(tert-butyl)-4-hydroxy-benzyl)malonate and bis[4-(1,1,3,3-tetramethylbutyl)phenyl]2,2-bis(3,5-di(tert-butyl)-4-hydroxybenzyl)malonate.

Hydroxybenzyl aromatic compounds, for example 1,3,5-tris(3,5-di(tert-butyl)-4-hydroxybenzyl)-2,4,6-trimethylbenzene, 1,4-bis(3,5-di(tert-butyl)-4-hydroxybenzyl)-2,3,5,6-tetramethylbenzene and 2,4,6-tris(3,5-di(tert-butyl)-4-hydroxybenzyl)phenol.

Triazine compounds, for example 2,4-bis(octylmercapto)-6-(3,5-di(tert-butyl)-4-hydroxyanilino)-1,3,5-triazine, 2-octylmercapto-4,6-bis(3,5-di(tert-butyl)-4-hydroxy-anilino)-1, 3,5-triazine, 2-octylmercapto-4,6-bis(3,5-di(tert-butyl)-4-hydroxyphenoxy)-1,3,5-triazine, 2,4,6-tris(3,5-di(tert-butyl)-4-hydroxyphenoxy)-1,2,3-triazine, 1,3,5-tris(3,5-di(tert-butyl)-4-hydroxybenzyl) isocyanurate, 1,3,5-tris(4-(tert-butyl)-3-hydroxy-2,6-dimethylbenzyl) isocyanurate, 2,4,6-tris(3,5-di(tert-butyl)-4-hydroxyphenylethyl)-1,3,5-triazine, 1,3,5-tris(3,5-di(tert-butyl)-4-hydroxyphenylpropionyl)hexahydro-1,3,5-triazine and 1,3,5-tris(3,5-dicyclohexyl-4-hydroxybenzyl) isocyanurate.

Benzylphosphonates, for example dimethyl 2,5-di(tert-butyl)-4-hydroxy-benzylphosphonate, diethyl 3,5-di(tert-butyl)-4-hydroxybenzylphosphonate ((3,5-bis(1,1-dimethylethyl)-4-hydroxyphenyl)methylphosphonic acid diethyl ester), dioctadecyl 3,5-di(tert-butyl)-4-hydroxybenzylphosphonate, dioctadecyl 5-(tert-butyl)-4-hydroxy-3-methylbenzylphosphonate and calcium salt of 3,5-di(tert-butyl)-4-hydroxybenzylphosphonic acid monoethyl ester.

Acylaminophenols, for example lauric acid 4-hydroxyanilide, stearic acid 4-hydroxyanilide, 2,4-bisoctylmercapto-6-(3,5-di-tert-butyl-4-hydroxyanilino)-s-triazine and octyl N-(3,5-di(tert-butyl)-4-hydroxyphenyl)carbamate.

Esters of β-(3,5-di(tert-butyl)-4-hydroxyphenyl)propionic acid with mono- or polyhydric alcohols, such as, e.g., with methanol, ethanol, n-octanol, isooctanol, octadecanol, 1,6- hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

Esters of β-(5-(tert-butyl)-4-hydroxy-3-methylphenyl) propionic acid with mono- or polyhydric alcohols, such as, e.g., with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

Esters of β-(3,5-dicyclohexyl-4-hydroxyphenyl)propionic acid with mono- or polyhydric alcohols, such as, e.g., with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

Esters of 3,5-di(tert-butyl)-4-hydroxyphenylacetic acid with mono- or polyhydric alcohols, such as, e.g., with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxalic acid diamide, 3-thiaundecanol, 3-thiapenta-decanol, trimethylhexanediol, trimethylolpropane and 4-hydroxymethyl-1-phospha-2,6,7-trioxabicyclo[2.2.2]octane.

Amides of β-(3,5-di(tert-butyl)-4-hydroxyphenyl)propionic acid, such as, e.g., N,N'-bis(3,5-di(tert-butyl)-4-hydroxyphenylpropionyl)hexamethylenediamide, N,N'-bis(3,5-di(tert-butyl)-4-hydroxyphenylpropionyl) trimethylenediamide, N,N'-bis(3,5-di(tert-butyl)-4-hydroxyphenylpropionyphydrazide and N,N'-bis[2-(3-[3,5-di(tert-butyl)-4-hydroxy-phenyl]propionyloxy)ethyl] oxamide (e.g. Naugard® XL-1 from Uniroyal).

Ascorbic Acid (Vitamin C)

Aminic antioxidants, such as N,N'-diisopropyl-p-phenylenediamine, N,N'-di(sec-butyl)-p-phenylenediamine, N,N'-bis(1,4-dimethylpentyl)-p-phenylenediamine, N,N'-bis (1-ethyl-3-methylpentyl)-p-phenylenediamine, N,N'-bis(1-methylheptyl)-p-phenylene-diamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-tolylsulfamoyl)-diphenylamine, N,N'-dimethyl-N,N'-di(sec-butyl)-p-phenylenediamine, diphenylamine, N-allyldiphenylamine, 4-isopropoxydiphenylamine, N-phenyl-1-naphthylamine, N-(4-(tert-octyl)phenyl)-1-naphthylamine, N-phenyl-2-naphthylamine, octylated diphenyl-amine, e.g. p,p'-di(tert-octyl)diphenylamine, 4-(n-butylamino)phenol, 4-butyrylamino-phenol, 4-nonanoylaminophenol, 4-dodecanoylaminophenol, 4-octadecanoylamino-phenol, bis(4-methoxyphenyl)amine, 2,6-di(tert-butyl)-4-dimethylaminomethylphenol, 2,4'-diamino-diphenylmethane, 4,4'-diaminodiphenylmethane, N,N,N', N'-tetramethyl-4,4'-diaminodiphenylmethane, 1,2-bis[(2-methylphenyl)amino]ethane, 1,2-bis(phenyl-amino)propane, (o-tolyl)biguanide, bis[4-(1',3'-dimethylbutyl)phenyl] amine, tert-octylated N-phenyl-1-naphthylamine, mixture of mono- and dialkylated tert-butyl/tert-octyldiphenylamines, mixture of mono- and dialkylated nonyldiphenylamines, mixture of mono- and dialkylated dodecyldiphenylamines, mixture of mono- and dialkylated isopropyl/isohexyldiphenylamines, mixture of mono- and dialkylated tert-butyldiphenyl-amines, 2,3-dihydro-3,3-dimethyl-4H-1,4-benzothiazine, phenothiazine, mixture of mono- and dialkylated tert-butyl/tert-octylphenothiazines, mixture of mono- and dialkylated tert-octylphenothiazines, N-allylphenothiazine, N,N,N',N'-tetraphenyl-1,4-diaminobut-2-ene, N,N-bis(2,2,6, 6-tetramethylpiperidin-4-yl)hexamethylenediamine, 2,2,6, 6-tetramethylpiperidin-4-one, 2,2,6,6-tetramethylpiperidin-4-ol, the dimethyl succinate polymer with 4-hydroxy-2,2,6, 6-tetramethyl-1-piperidinethanol [CAS number 65447-77-0] (for example Tinuvin® 622 from Ciba Specialty Chemicals Inc.) and the polymer of 2,2,4,4-tetramethyl-7-oxa-3,20-diazadispiro[5.1.11.2]heneicosan-21-one and epichlorohydrin [CAS No.: 202483-55-4] (for example Hostavin® N 30 from Clariant.).

The group i) of the nickel compounds includes, for example, nickel complexes of 2,2'-thiobis[4-(1,1,3,3-tetramethylbutyl)phenol], such as the 1:1 or 1:2 complex, if appropriate with additional ligands, such as n-butylamine, triethanolamine, or N-cyclohexyldiethanolamine, nickel dibutyldithiocarbamate, nickel salts of monoalkyl 4-hydroxy-3,5-di-tert-butylbenzylphosphonates, e.g. the methyl or ethyl ester, nickel complexes of ketoximes, e.g. of 2-hydroxy-4-methylphenyl undecyl ketoxime, nickel complex of 1-phenyl-4-lauroyl-5-hydroxypyrazole, if appropriate with additional ligands.

The group j) of the sterically hindered amines includes, for example, 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl) sebacate, bis(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) (n-butyl)(3, 5-di(tert-butyl)-4-hydroxybenzyl)malonate, bis(1,2,2,6,6-pentamethylpiperidyl) n-butyl-3,5-di-tert-butyl-4-hydroxybenzylmalonate condensation product of 1-(2-hydroxyethyl)-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-(tert-octylamino)-2,6-dichloro-1,3,5-triazine, tris(2,2, 6,6-tetramethyl-4-piperidyl) nitrilotriacetate, tetrakis(2,2,6, 6-tetramethyl-4-piperidyl) 1,2,3,4-butanetetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6, 6-tetramethylpiperidine, bis(1,2,2,6,6-pentamethyl-4-piperidyl) 2-(n-butyl)-2-(2-hydroxy-3,5-di(tert-butyl)benzyl) malonate, 3-(n-octyl)-7,7,9,9-tetramethyl-1,3,8-triazaspiro [4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensation products of N,N'-bis(2,2,6,6-tetramethyl-4-piperidyl)hexamethylenediamine and 4-morpholino-2,6-dichloro-1,3,5-triazine, condensation product of 2-chloro-4,6-bis(4-n-butyl-amino-2,2,6,6-tetramethylpiiperidyl)-1,3,5-triazine and 1,2-bis(3-aminopropylamino)ethane, condensation product of 2-chloro-4,6-di(4-(n-butyl)amino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyppyrrolidine-2,5-dione, 3-dodecyl-1-(1,2,2,6,6-pentamethyl-4-piperidyl)pyrrolidine-2,5-dione, mixture of 4-hexadecyloxy- and 4-stearyloxy-2,2,6,6-tetramethylpiperidine, condensation product of N,N'-bis(2,2,6,6-tetramethyl-4-piperidyl)hexamethylenediamine and 4-cyclohexylamino-2,6-dichloro-1,3,5-triazine, condensation product of 1,2-bis(3-aminopropylamino)ethane and 2,4,6-trichloro-1,3,5-triazine, and also 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, reaction product of 7,7,9,9-tetramethyl-2-cycloundecyl-1-oxa-3,8-diaza-4-oxospiro[4,5]decane and epichlorhydrin, 1,1-bis(1,2,2,6,6-pentamethyl-4-piperidyloxycarbonyl)-2-(4-methoxyphenyl)ethene, diester of 4-methoxymethylenemalonic acid with 1,2,2,6,6-pentamethyl-4-hydroxy-piperidine, poly[methylpropyl-3-oxo-4-(2,2,6,6-tetramethyl-4-piperidyl)]siloxane, 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine and a hydrocarbon moiety of tert-amyl alcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl) sebacate, bis(1-(2-hydroxy-2-methylpropoxy)-2,2,6,6-tetramethylpiperidin-4-yl) adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl) glutarate, 2,4-bis{N[1-(2-hydroxy-2-methylpropoxy)-2,2,6,6-tetramethylpiperidin-4-yl]-N-butylamino}-6-(2hydroxyethylamino)-s-triazine, hexahydro-2,6-bis(2,2,6,6-tetramethyl-4-piperidyl)-1H,4H,5H,8H-2,3a,4a,6,7a,8a-hexaazacyclopenta[def]fluorene-4,8-dione (z. B. Uvinul® 4049 from BASF AG, Ludwigshafen), poly[[6[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] [CAS No. 71878-19-8], 1,3,5-triazine-2,4,6-triamine, N,N'''-[1,2-ethanediylbis [[4,6-bis-[butyl(1,2,2,6,6-pentamethyl-4-piperidinyl)amino]-1,3,5-triazin-2-yl]imino]-3,1-propanediyl]]bis[N',N''-dibutyl-N', N''-bis(1,2,2,6,6-pentamethyl-4-piperidinyl)—(CAS No. 106990-43-6) (e.g. Chimassorb 119 from Ciba Specialty Chemicals, Inc.).

The group k) of the metal deactivators includes, for example, N,N'-diphenyloxamide, N-salicylal-N'-salicyloylhydrazine, N,N'-bis(salicyloyl)hydrazine, N,N'-bis(3,5-di (tert-butyl)-4-hydroxyphenylpropionyl)hydrazine, 3-salicyloylamino-1,2,4-triazole, the bis(benzylidene) derivative of oxalic dihydrazide, oxanilide, isophthalic dihydrazide, sebacic bisphenylhydrazide, N,N'-diacetyladipic acid dihydrazide, N,N'-bis(salicyloyl)-oxalic acid dihydrazide or N,N'-bis(salicyloyl)thiopropionic dihydrazide.

The group l) of the phosphites and phosphonites includes, for example, triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di(tert-butyl)phenyl) phosphite, diisodecyl pentaerythritol diphosphite, bis(2,4-di(tert-butyl)phenyl) pentaerythritol diphosphite, bis(2,6-di(tert-butyl)-4-methylphenyl) pentaerythritol diphosphite, diisodecyloxy pentaerythritol diphosphite, bis(2,4-di(tert-butyl)-6-methylphenyl) pentaerythritol diphosphite, bis(2,4,6-tris(tert-butyl)phenyl) pentaerythritol diphosphite, tristearyl sorbitol triphosphite, tetrakis(2,4-di(tert-butyl)phenyl) 4,4'-biphenylenediphosphonite, 6-isooctyloxy-2,4,8,10-tetra(tert-butyl)dibenzo[d,f][1,3,2]dioxaphosphepin, 6-fluoro-2,4,8,10-tetra(tert-butyl)-12-methyldibenzo[d,g][1,3,2]dioxaphosphocin, bis(2,4-di(tert-butyl)-6-methylphenyl)methyl phosphite, bis(2,4-di(tert-butyl)-6-methylphenyl)ethyl phosphite, 2,2',2''-nitrilo[triethyl-tris(3,3',5,5'-tetra (tert-butyl)-1,1'-biphenyl-2,2'-diyl) phosphite] and 2-ethylhexyl (3,3',5,5'-tetra(tert-butyl)-1,1'-biphenyl-2,2'-diyl) phosphite.

The group m) of the hydroxylamines includes, for example, N,N-dibenzylhydroxyl-amine, N,N-diethylhydroxylamine, N,N-dioctylhydroxylamine, N,N-dilauryl-hydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecylhydroxylamine and N,N-dialkylhydroxylamine from hydrogenated tallow fatty amines.

The group n) of the nitrones includes, for example, N-benzyl-α-phenylnitrone, N-ethyl-α-methylnitrone, N-octyl-α-heptylnitrone, N-lauryl-α-undecylnitrone, N-tetradecyl-α-tridecylnitrone, N-hexadecyl-α-pentadecylnitrone, N-octadecyl-α-heptadecylnitrone, N-hexadecyl-α-heptadecylnitrone, N-octadecyl-α-pentadecylnitrone, N-heptadecyl-α-heptadecylnitrone, N-octadecyl-α-hexadecylnitrone, N-methyl-α-heptadecylnitrone and nitrones derived from N,N-dialkylhydroxylamines prepared from hydrogenated tallow fatty amines.

The group o) of the amine oxides includes, for example, amine oxide derivatives as disclosed in U.S. Pat. Nos. 5,844,029 and 5,880,191, didecylmethylamine oxide, tridecylamine oxide, tridodecylamine oxide and trihexadecylamine oxide.

The group p) of the benzofuranones and indolinones includes, for example, those disclosed in U.S. Pat. Nos. 4,325,863, 4,338,244, 5,175,312, 5,216,052 or 5,252,643, in DE-A-4316611, in DE-A-4316622, in DE-A-4316876, in EP-A-0589839 or in EP-A-0591102 or 3-[4-(2-acetoxyethoxy) phenyl]-5,7-di(tert-butyl)benzofuran-2-one, 5,7-di(tert-butyl)-3-[4-(2-stearoyloxyethoxy)phenyl]benzofuran-2-one, 3,3'-bis[5,7-di(tert-butyl)-3-(4-[2-hydroxyethoxy]phenyl) benzofuran-2-one], 5,7-di(tert-butyl)-3-(4-ethoxyphenyl) benzofuran-2-one, 3-(4-acetoxy-3,5-dimethylphenyl)-5,7-di (tert-butyl)benzofuran-2-one, 3-(3,5-dimethyl-4-pivaloyloxyphenyl)-5,7-di(tert-butyl)benzofuran-2-one, 3-(3,4-dimethylphenyl)-5,7-di(tert-butyl)benzofuran-2-one, Irganox® HP-136 from Ciba Specialty Chemicals and 3-(2,3-dimethylphenyl)-5,7-di(tert-butyl)benzofuran-2-one.

The group q) of the thiosynergists includes, for example, dilauryl thiodipropionate or distearyl thiodipropionate.

The group r) of the peroxide-destroying compounds includes, for example, esters of β-thiodipropionic acid, e.g. the lauryl, stearyl, myristyl or tridecyl ester, mercaptobenzimidazole or the zinc salt of 2-mercaptobenzimidazole, zinc dibutyl-dithiocarbamate, dioctadecyl disulfide or pentaerythritol tetrakis(3-dodecylmercapto-propionate).

The group s) of the basic costabilizers includes, for example, melamine, polyvinyl-pyrrolidone, dicyandiamide, triallyl cyanurate, urea derivatives, hydrazine derivatives, amines, polyamides, polyurethanes, the alkali metal and alkaline earth metal salts of higher fatty acids, e.g. calcium stearate, zinc stearate, magnesium behenate, magnesium stearate, sodium ricinoleate, and potassium palmitate, antimony pyrocatecholate or zinc pyrocatecholate.

The inventive mixture can moreover comprise, as component (d), or the plastic can comprise, other additives. Suitable additives of group t) which can be used are the conventional additives such as pigments, dyes, nucleating agents, fillers or reinforcing agents, antifogging agents, biocides, and antistatic agents.

Suitable pigments are inorganic pigments, for example the three crystalline forms of titanium dioxide: rutile, anatase, or brookite, or ultramarine blue, iron oxides, bismuth vanadates, or carbon black, or else the class of organic pigments, for example compounds from the class of the phthalocyanines, perylenes, azo compounds, isoindolines, quinophthalones, diketopyrrolopyrroles, quinacridones, dioxazines, and indanthrones.

Dyes are any of the colorants which in the plastic used undergo complete dissociation or are present with molecular dispersion and thus can be used to provide highly transparent, non-scattering coloration of polymers. Dyes are also considered to include organic compounds which fluoresce in the visible portion of the electromagnetic spectrum, examples being fluorescent dyes.

Suitable nucleating agents comprise, for example, inorganic substances such as talc, metal oxides, such as titanium dioxide or magnesium oxide, phosphates, carbonates, or sulfates, preferably of alkaline earth metals; organic compounds, such as mono- or polycarboxylic acids, and also their salts, e.g. 4-tert-butylbenzoic acid, adipic acid, diphenylacetic acid, sodium succinate, or sodium benzoate; polymeric compounds, such as ionic copolymers ("ionomers").

Suitable fillers or reinforcing materials comprise, for example, calcium carbonate, silicates, talc, mica, kaolin, barium sulfate, metal oxides and metal hydroxides, carbon black, graphite, wood flour, and flours or fibers of other natural products, and synthetic fibers. Other examples of fibrous or pulverant fillers that may be used are carbon fibers or glass fibers in the form of glass textiles, glass mats, or glass silk rovings, chopped glass, or glass beads, and also Wollastonite. The form in which glass fibers are incorporated can either be that of short glass fibers or else that of continuous-filament fibers (rovings).

Examples of suitable antistatic agents are amine derivatives, such as N,N-bis(hydroxyalkyl)alkylamines or -alkyleneamines, polyethylene glycol esters, polyethylene glycol ethers, ethoxylated carboxylic esters, ethoxylated carboxamides, and glycerol mono- and distearates, and also their mixtures.

Examples which may be mentioned of plastics which can be stabilized by the inventive mixtures are:
thermoplastic elastomers;
polymers of mono- and diolefins, for example low- and high-density polyethylene, polypropylene, linear poly-1-butene, polyisoprene, polybutadiene, and also copolymers of mono- or diolefins, or a mixture of the polymers mentioned;
copolymers of mono- or diolefins with other vinyl monomers, for example ethylene-alkyl acrylate copolymers, ethylene-alkyl methacrylate copolymers, ethylene-vinyl acetate copolymers, or ethylene-acrylic acid copolymers;
polystyrene, and also copolymers of styrene or α-methylstyrene with dienes and/or with acrylic derivatives, for example styrene-butadiene, styrene-acrylonitrile (SAN), styrene-ethyl methacrylate, styrene-butadiene-ethyl acrylate, styrene-acrylonitrile-methacrylate, acrylonitrile-butadiene-styrene (ABS), or methyl methacrylate-butadiene-styrene (MBS);
Halogen-comprising polymers, for example polyvinyl chloride, polyvinyl fluoride, polyvinylidene fluoride, and also their copolymers;
polymers which derive from α,β-unsaturated acids and from their derivatives, for example polyacrylates, polymethacrylates, polyacrylamides, and polyacrylonitriles;
polymers which derive from unsaturated alcohols and amines or from their acrylic derivatives or acetals, for example polyvinyl alcohol and polyvinyl acetate;
polyurethanes, polyamides, polyureas, polyesters, polycarbonates, polysulfones, polyether sulfones, and polyether ketones.

It is also possible to use the inventive mixtures to stabilize coatings, for example industrial coatings. Among these, particular emphasis should be given to baking enamel systems, and among these in turn to vehicle paint systems, preferably two-layer paint systems. An example of another application sector is paints for exterior paintwork on buildings, or on other structures, or on industrial apparatuses.

The inventive mixtures can be added in solid or dissolved form to the coating. Their good solubility in coating systems is particularly advantageous here.

The inventive mixtures are preferably used for the stabilization of thermoplastic elastomers, for example polyolefin-based thermoplastic elastomers. The inventive mixtures are in particular used in the stabilization of molding compositions composed of the materials mentioned.

Another preferred field of use is the stabilization of low- and high-density polyethylene, and also of polypropylene and polyamide, and by way of example also of fibers composed thereof.

The inventive mixtures exhibit improved stabilization of non-living organic material with respect to light with high UV content and/or with high light intensity. The inventive mixtures are moreover based on starting materials that are easy to obtain. With the aid of the inventive mixtures it is possible to provide efficient protection of non-living organic material with respect to oxygen or heat.

The above embodiments of the inventive process, and the examples below, provide examples of illustration of the present invention. However, many other variations of the process, and combinations of the features of the inventive process, are conceivable by the person skilled in the art, without exceeding the scope of the patent claims.

EXAMPLES

TPO plaques based on polyolefin-based thermoplastic elastomer (polypropylene, AW161C, "reactor grade" TPO from Sumitomo Chemical Industries Co., Ltd.)

Example 1

Preparation of the Inventive Mixtures 1a) 100 g of poly-{3-(eicosyltetracosyl)-1-[2,2,6,6-tetramethylpiperidin-4-yl]-pyrrolidine-2,5-dione} (CAS No. 152261-33-1; HALS Ia) were melted by heating and 50 g of hexadecyl-3,5-di-ten-butyl-4-hydroxybenzoate (IIIa) were admixed. After homogenization, pastilles were molded from the hot mixture and solidified on cooling. 1b) 40 g of N,N'-bisformyl-N,N'-bis(2,2,6,6-tetramethyl-4-piperidinyl)-hexa-methylenediamine (IIa) and 20 g of 2,4-di-ten-butylphenyl 3,5-di-tert-butyl-4-hydroxybenzoate were intimately combined in a tumbling mixer.

Example 2

Synergistic Action of the Mixture in Comparison with the Individual Components Beige-colored TPO plaques with various stabilizers were produced and then weathered to SAE J 1885. The color change (ΔE) was measured after 450 MJ/m² of irradiation. The tables below give the results (where a smaller color change indicates better results):

| | Stabilizer system | ΔE after 450 MJ/m² |
|---|---|---|
| 1 | 0.15% of HALS Ia | 5.3 |
| 2 | 0.1% of HALS Ia<br>0.05% benzoate IIIb | 4.4 |

| | Stabilizer system | ΔE after 450 MJ/m² |
|---|---|---|
| 1 | 0.075% of HALS Ia<br>0.075% of HALS IIa | 3.9 |
| 2 | 0.05% of HALS Ia<br>0.05% of HALS IIa<br>0.05% of benzoate IIIa | 0.2 |

It can be seen that the inventive mixtures (in each case No. 2) exhibit better results than the corresponding comparative examples (in each case No. 1) using (mixtures of) HALS compounds.

Example 3

Retention of Gloss on Colored TPO Plaques

Beige-colored TPO plaques with various stabilizers were produced and then weathered to SAE J 1885. Retention of gloss (at an angle of 60°) was measured after 150 and 300 MJ/m² of irradiation. Gloss is a measure of the smoothness of the surfaces. When the surface is degraded it becomes rough, and the gloss values falls. The tables below give the results:

| | Stabilizer system | Gloss (60°), reference | Gloss (60°) after 150 MJ/m² | Gloss (60°) after 300 MJ/m² |
|---|---|---|---|---|
| 1 | 0.1% of HALS Ia<br>0.05% of benzoate IIIb | 72.2 | 51.8 | 4.8 |
| 2 | 0.1% of HALS IIa<br>0.05% of benzoate IIIb | 69.5 | 62.7 | 55.2 |
| 3 | 0.05% of HALS Ia<br>0.05% of HALS IIa<br>0.05% of benzoate IIIb | 73.9 | 57.6 | 48.8 |
| 4 | 0.1% of HALS IV*<br>0.05% of benzoate IIIb | 70.4 | 13.0 | 2.3 |
| 5 | 0.1% of HALS V*<br>0.05% of benzoate IIIb | 71.7 | 7.1 | 2.3 |

*HALS IV is poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]]) (CAS No. 71878-19-8, Chimassorb 944); HALS V is N,N'''-[1,2-ethanediylbis [[[4,6-bis[butyl(1,2,2,6,6-pentamethyl-4-piperidinyl)amino]-1,3,5-triazin-2-yl]imino]-3,1-propanediyl]]bis[N',N''-dibutyl-N',N''-bis(1,2,2,6,6-pentamethyl-4-piperidinyl)-1,3,5-triazine-2,4,6-triamine (CAS-No. 106990-43-6, Chimassorb 199).

The present results clearly show that the inventive mixtures of HALS and benzoate (Nos. 1-3) exhibit good stabilizing action when comparison is made with the comparative examples using HALS IV (No. 4) and HALS V (No. 5).

The invention claimed is:
1. A mixture, comprising at least one of (a) and (b), and further comprising (c) and (d):
   (a) an oligomeric compound, comprising a repeat unit of general formula (I) or an acid-addition salt thereof

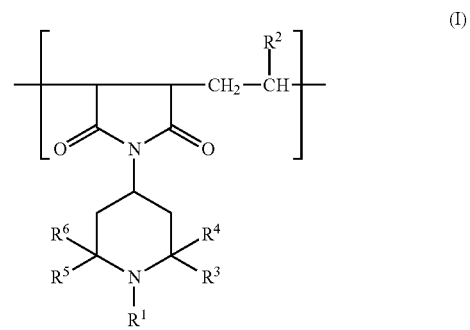

in which
$R^1$ is $C_1$-$C_6$ alkoxy,
$R^2$ is H or $C_1$-$C_{30}$-alkyl,
$R^3$, $R^4$, $R^5$, and $R^6$, is $CH_3$,
   (b) a compound of general formula (II) or an acid-addition salt thereof

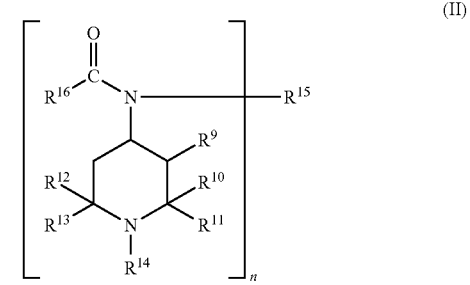

in which
n is 2,
$R^9$ is H,
$R^{10}$, $R^{11}$, $R^{12}$, and $R^{13}$, is $CH_3$,
$R^{14}$ is formyl, acyl or benzyl,
$R^{16}$ is H,
$R^{15}$ is $C_2$-$C_{22}$-alkylene,
   (c) at least one compound of general formula (III)

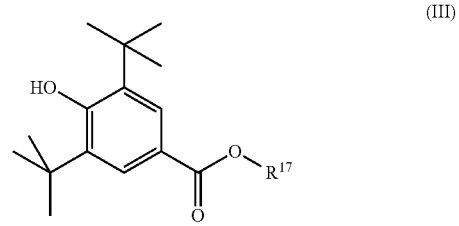

In which
$R^{17}$ is $C_1$-$C_{20}$-alkyl or substituted phenyl,
and
   (d) optionally further additives,
wherein
each of the substituents $R^1$ to $R^{17}$ has interruption at any desired position by one or more heteroatoms, where the number of the heteroatoms is not more than 10, and optionally each of the substituents $R^1$ to $R^{17}$ has substitution at any desired position, but not more than five times, by $C_1$-$C_{30}$-alkyl, $C_1$-$C_{20}$-alkoxy, aryl, heterocyclic moieties, heteroatoms, or halogen, and the likewise has substitution at most twice, by the substituents or by substituted aryl moieties, and wherein a ratio by weight of the at least one of components (a) and (b) to component (c) is from 10:1 to 1:2.

2. The mixture according to claim 1, wherein (d) is present and comprises an antioxidant.

3. The mixture according to claim 1, wherein component (a) comprises an oligomeric compound having a repeat unit of the general formula (I), wherein $R^2$=$C_{16}$-$C_{26}$-alkyl.

4. The mixture according to claim 1, wherein component (a) comprises a compound of the general formula (I), wherein $R^2$ is a hydrogen atom or $C_2$-$C_{10}$-alkyl.

5. The mixture according to claim 1, wherein component (c) comprises a compound of the general formula (III), where $R^{17}$=$C_{16}$-alkyl.

6. The mixture according to claim 1, wherein component (c) comprises a compound of the general formula (III), where $R^{17}$=2,4-di-tert-butylphenyl.

7. The mixture according to claim 1, wherein the mixture is capable of stabilizing a non-living organic material with respect to exposure to at least one of light, oxygen, and heat.

8. The mixture according to claim 7, wherein the non-living organic material comprises at least one polymer selected from the group consisting of thermoplastic elastomers, polyolefins, polystyrene, copolymers of styrene or of α-methylstyrene, polyesters, polycarbonates, polyvinyl chloride, polyacrylates, polymethacrylates, polyurethanes, and physical blends thereof.

9. The mixture according to claim 8, the non-living organic material is an olefin-based thermoplastic elastomer.

10. A non-living organic material, comprising at least one mixture according to claim 1.

11. An article, produced from the non-living organic material according to claim 10.

12. A process for stabilizing a non-living organic material with respect to exposure to at least one of light, oxygen, and heat, comprising adding an effective amount of at least one mixture according to claim 1 to the non-living organic material.

13. The mixture according to claim 1, wherein component (a) is present.

14. The mixture according to claim 1, wherein component (b) is present.

15. The mixture according to claim 1, wherein component (a) and component (b) are present.

* * * * *